US00PP10591P

United States Patent [19]

Kramer

[11] Patent Number: Plant 10,591

[45] Date of Patent: Sep. 8, 1998

[54] HEATHER PLANT NAMED 'AMETHYST'

[76] Inventor: Kurt Kramer, Edammer Str. 26, 26188 Edewecht, Germany

[21] Appl. No.: 870,282

[22] Filed: Jun. 6, 1997

[51] Int. Cl.[6] ..... A01H 5/00

[52] U.S. Cl. ..... Plt./54.1

[58] Field of Search ..... Plt./54.1

[56] References Cited

U.S. PATENT DOCUMENTS

P.P. 9,710 11/1996 Kramer ..... Plt./54.1

*Primary Examiner*—James R. Feyrer
*Assistant Examiner*—Kent L. Bell
*Attorney, Agent, or Firm*—C. A. Whealy

[57] ABSTRACT

A distinct cultivar of Heather plant named 'Amethyst', characterized by its dark purple flower buds; upright plant habit which allows for ease of mechanical pruning; freely branching habit; strong stems; and good keeping quality at low temperatures.

2 Drawing Sheets

The present invention relates to a new and distinct cultivar of Heather plant, botanically known as *Calluna vulgaris,* and hereinafter referred to by the cultivar name 'Amethyst'.

The new Heather is a product of a planned breeding program conducted by the inventor in Edewecht, Germany. The objective of the breeding program was to create new Heather cultivars having an upright growth habit and a long flowering time.

The new Heather originated from a cross made by the inventor of the inventor's proprietary Heather seedling selections. The male, or pollen, parent is identified as number 88-49-2 and the female, or seed, parent is identified as number 88-49-1. The cultivar 'Amethyst' was discovered and selected by the inventor in September, 1990, as a flowering plant within the progeny of this cross in a controlled environment in Edewecht, Germany.

Asexual reproduction of the new Heather by terminal cuttings taken at Edewecht, Germany, has shown that the unique features of this new Heather are stable and reproduced true to type in successive generations.

The following traits have been repeatedly observed and are determined to be the unique characteristics of 'Amethyst'. These characteristics in combination distinguish 'Amethyst' as a new and distinct cultivar:

1. Dark purple flower buds.
2. Upright plant habit which allows for ease of mechanical pruning.
3. Freely branching habit.
4. Strong stems.
5. Good keeping quality at low temperatures.

The new Heather has not been observed under all possible environmental conditions. The phenotype may vary somewhat with variations in environment such as temperature and light intensity, without, however, any variance in genotype.

The following characteristics differentiate the new Heather from other Heathers commercially know and used, namely the cultivar 'Alexandra' (disclosed in U.S. Plant Pat. (No. 9,710):

1. Plants of the new Heather are more upright than plants of the cultivar 'Alexandra'. Plants of the new Heather are easier to prune mechanically than plants of the cultivar 'Alexandra'.
2. Plants of the new Heather develop flower buds later than plants of the cultivar 'Alexandra'.
3. Plants of the new Heather have slightly smaller flower buds than plants of the cultivar 'Alexandra'.
4. Flower bud color of plants of the new Heather is darker purple than flower bud color of plants of the cultivar 'Alexandra'.

5. Plants of the new Heather tolerate low temperatures, that is, −8° C, better than plants of the cultivar 'Alexandra'.

The accompanying colored photographs illustrate the overall appearance of the new cultivar, showing the colors as true as it is reasonably possible to obtain in colored reproductions of this type.

The first photograph comprises a top perspective view of a typical plant of 'Amethyst'.

The second photograph comprises a close-up view of mature flower buds. The flower and foliage colors in these photographs appear different than the actual colors due to light reflectance.

In the following description, color references are made to The Royal Horticultural Society Colour Chart except where general terms of ordinary dictionary significance are used. The following observations and measurements describe plants grown in Edewecht, Germany, under commercial field conditions.

Botanical classification: *Calluna vulgaris* cultivar 'Amethyst'.

Commercial classification: Broom Heather.

Parentage:

*Male, or pollen, parent.*—Inventor's proprietary Heather seedling selection number 88-49-2.

*Female, or seed, parent:—Inventor's proprietary Heather seedling selection number* 88-49-1.

Propagation:

*Type.*—Terminal tip cuttings.

*Time to rooting.*—About 30 and 40 days with soil temperatures of 25 and 18° C, respectively.

*Rooting habit.*—Fibrous and freely branching.

Plant description:

*Appearance.*—Generally low mounded, basally-branched shrub, very freely branching. Flower spikes arise at terminal apices. Numerous axillary branches below flower spikes. Appropriate for 500-ml to 3-liter containers.

*Plant height from soil level to top of plant plane.*—About 16 cm.

*Growth rate.*—Moderate to rapid.

*Vigor.*—Moderate to high.

*Crop time.*—About 14 months are required from unrooted cuttings to finishing in a 10 to 15-cm container. Plants are generally grown without supplemental heat and pruned twice during production.

*Foliage description.*—Opposite, scale-like and bractiolate, sessile, arranged on stems which are roughly square in cross-section. Size: Length: 1 to 2 mm. Width: 0.3 to 0.8 mm. Color: Mature foliage is darker green than 147A.

Flower Description:

*Appearance.*—Flowers formed at the terminals of main branches. Flower spikes have numerous uniformly-spaced auxiliary verticils with clusters of 2 to 4, or more, mature buds outwardly radiating from the apex of oppositely-placed, short branches arising from leaf axils. Length of spikes is normally about 10 to 13 cm. The number of buds formed is about average for the species. Flower buds do not open to a flower, but rather remain in the bud stage. The corolla and the reproductive organs of the new Heather are identical to those of the species.

*Flowering habit.*—Recurrent.

*Natural flowering season.*—The new Heather produces flower buds in the fall (September through November) and remain in the bud stage for about 6 months, or until early spring.

*Flower bud description.*—Shape: Elliptic. Size: Length: About 5 mm. Diameter: 1 to 2 mm. Color: 61A/71A.

Disease resistance: No known resistance to Heather diseases has been observed to date on plants grown under commercial conditions. Infection with *Glormorella cingulata* and *Botrytis cinerea* is possible.

Seed production:

The new Heather does not produce seed because the style is covered by the sepals.

It is claimed:

1. A new and distinct cultivar of Heather plant named Amethyst, as illustrated and described.

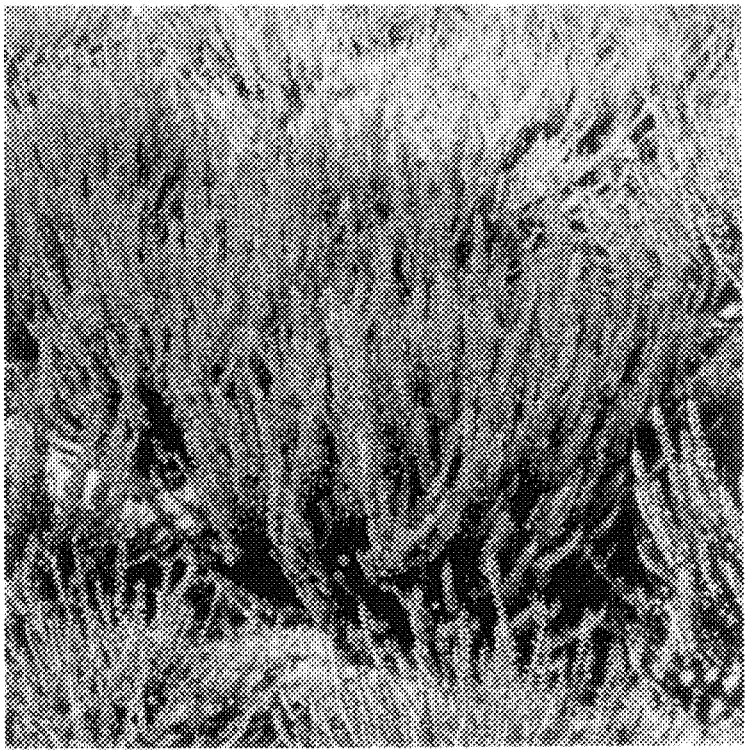

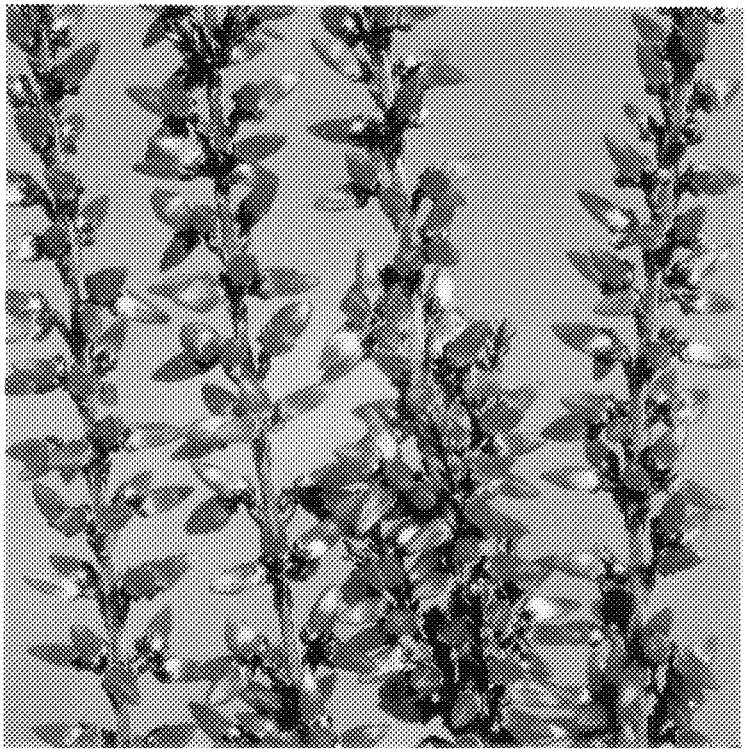

* * * * *